(12) United States Patent
Clark et al.

(10) Patent No.: US 6,558,389 B2
(45) Date of Patent: May 6, 2003

(54) ENDOSTEAL TIBIAL LIGAMENT FIXATION WITH ADJUSTABLE TENSIONING

(76) Inventors: Ron Clark, 4805 Lakeridge Ct., Valparaiso, IN (US) 46383; Raymond E. Olsen, 190 Summit Dr., Smithfield, UT (US) 84335

( * ) Notice: Subject to any disclaimer, the term of this patent is extended or adjusted under 35 U.S.C. 154(b) by 0 days.

(21) Appl. No.: 09/846,552

(22) Filed: Apr. 30, 2001

(65) Prior Publication Data

US 2002/0065528 A1 May 30, 2002

Related U.S. Application Data

(63) Continuation of application No. 09/734,315, filed on Nov. 30, 2000, now abandoned.
(60) Provisional application No. 60/168,066, filed on Nov. 30, 1999.

(51) Int. Cl.[7] .............................................. A61B 17/56
(52) U.S. Cl. ............................ 606/72; 606/60; 606/232
(58) Field of Search ........................... 606/72, 74, 151, 606/213, 232, 73; 411/338, 339, 508, 509, 510, 485, 456; 623/13.11, 13.12, 13.13, 13.14

(56) References Cited

U.S. PATENT DOCUMENTS

| | | | |
|---|---|---|---|
| 1,890,348 A | * | 12/1932 | Weatherhead, Jr. |
| 4,708,132 A | | 11/1987 | Mahony, III |
| 4,711,232 A | | 12/1987 | Hunt et al. |
| 4,716,893 A | | 1/1988 | Fischer et al. |
| 4,772,286 A | | 9/1988 | Goble et al. |
| 4,778,468 A | | 10/1988 | Silvestrini |
| 4,796,612 A | * | 1/1989 | Reese |
| 4,870,957 A | | 10/1989 | Goble et al. |
| 5,207,404 A | * | 5/1993 | Reinhard .................. 248/217.4 |
| 5,282,802 A | | 2/1994 | Mahony, III |
| 5,370,661 A | * | 12/1994 | Branch ........................ 606/232 |
| 5,478,353 A | * | 12/1995 | Yoon ........................... 606/213 |
| 5,782,866 A | * | 7/1998 | Wenstrom, Jr. ............. 606/232 |
| 5,871,504 A | * | 2/1999 | Eaton et al. ................. 606/232 |
| 5,931,840 A | * | 8/1999 | Gobel et al. ................... 606/73 |
| 6,162,234 A | | 12/2000 | Freedland et al. |
| 6,270,304 B1 | | 8/2001 | Freedland |
| 6,283,996 B1 | * | 9/2001 | Chervitz et al. ......... 623/13.14 |

OTHER PUBLICATIONS

F. Alan Barber, M.D.; Flipped Patellar Tendon Anterior Cruciate Ligament Reconstruction; Anthroscopy: The Journal of Arthroscopic and Related Surgery, vol. 16, No. 5 (Jul.–Aug.), 2000: pp 483–490.

* cited by examiner

Primary Examiner—David O. Reip
(74) Attorney, Agent, or Firm—Clayton, Howarth & Cannon, P.C.

(57) ABSTRACT

A system for endosteal tibial ligament fixation with adjustable tensioning is disclosed. A grasping hook located on a shaft is used to draw a ligament graft into a contoured drill hole formed in a bone. A series of slanted ridges on the shaft can pass in only one direction through a securing push nut residing in the contoured drill hole, resulting in an interference fit that secures the attachment system, while allowing the tension of the ligament graft to be adjusted.

3 Claims, 9 Drawing Sheets

ENDOSTEAL TIBIAL LIGAMENT FIXATION WITH ADJUSTABLE TENSIONING

CROSS-REFERENCE TO RELATED APPLICATIONS

This application is a continuation of U.S. patent application Ser. No. 09/734,315, filed Nov. 30, 2000, now abandoned, which application claims the benefit of U.S. Provisional Application No. 60/168,066, filed Nov. 30, 1999, entitled "ENDOSTEAL TIBIAL LIGAMENT FIXATION WITH METHOD OF ADJUSTABLE TENSIONING." These related applications are each hereby incorporated by reference herein in their entireties, including but not limited to those portions that specifically appear hereinafter.

STATEMENT REGARDING FEDERALLY SPONSORED RESEARCH OR DEVELOPMENT

Not Applicable.

BACKGROUND OF THE INVENTION

1. The Field of the Invention

The present invention relates generally to ligament and tendon graft attachment devices, and more particularly, but not necessarily entirely, to a ligament fixation system having adjustable tightening qualities.

2. Description of Related Art

This invention relates to tibial fixation for anterior or posterior cruciate ligament reconstruction of the knee. Current practice involves the use of screws, staples, spiked washers, or suture buttons to secure a ligament substituted to the tibia. The ability to secure the ligament substituted within the bone (endosteal) is known in the prior art.

Apparatus and methods for attaching ligaments to bone have been developed and are preexisting in the prior art. Typically, these devices either attach a ligament graft to the exterior of a bone, or within a drill hole bored through the endosteal portion of the bone. The strength of the graft attachment in such systems is usually dependent on the cancellous bone density of the bone.

There are several other ligament fixation devices known in the prior art, such as that disclosed in U.S. Pat. No. 4,870,957 (the "'957 patent"), which is incorporated by reference herein in its entirety. The device disclosed in the '957 patent features an eyelet attached to a stud. A ligament graft is placed into the eyelet by looping the graft and passing the looped graft through a channel in the stud to the eyelet. The stud is then passed into a drill hole bored into the bone. A threaded footing is placed in the drill hole, disposed on threads tapped into the walls defining the drill hole. The stud is seated within a portion of the threaded footing in a type of rotational interference fit, and the threaded footing is then turned on the tapped threads until a desired ligament tension is reached. This system thus requires the drill hole in the bone to be threaded, an additional surgical procedure that introduces the potential of the bone threads stripping or being misaligned. It further requires the stud to be placed into the drill hole from the same direction in which the ligament graft enters, increasing the complexity of the surgery and the number of items that must pass through the joint across which the ligament passes. An additional limiting factor is that the device can only be used with grafts that are formed into loops. The device shown in the '957 patent thus would not be suitable for use with bone-tendon-bone (BTB) implants, including the recent anterior cruciate ligament (ACL) reconstruction technique that involves flipping one end of a patellar tendon autograft (PTA), details of which are described in Barber, A. F., Flipped Patellar Tendon Autograft Anterior Cruciate Ligament Reconstruction, *Arthroscopy: The Journal of Arthroscopic and Related Surgery*, Vol. 16. No. 5, pp 483–490, (July–August, 2000), which is hereby incorporated by reference herein in its entirety.

Implanting a BTB ligament graft has been traditionally accomplished by inserting the graft into a drill hole bored into a bone, and by inserting a screw next to the bone plug of the graft to compress the bone plug against the wall of the drill hole. Examples of this technique are found in Barber (cited above), and in U.S. Pat. No. 5,282,802, which is hereby incorporated by reference herein in its entirety. Since the graft is held in place by frictional engagement between the bone plug and the wall of the drill hole, the strength of the attachment is proportional to the density of the bone. Additionally, the screw must be placed against the cancellous side of the bone plug, rather than the cortical side, to reduce the chances of graft pullout. Such factors limit the positions in which the bone plug may be rotated. Such fixation factors also do not allow for simple adjustment of the graft tension.

Other prior art devices operate either by holding a graft within a bone channel by compressing a pretensioned graft between its own components, such as that disclosed in U.S. Pat. No. 4,708,132 to Silvestrini, which is incorporated by reference in its entirety, or by attaching the graft to connectors located on the exterior surface of the bone, such as that disclosed in U.S. Pat. No. 4,778,468 to Hunt et al., or U.S. Pat. No. 4,772,286 to Goble et al., each of which is incorporated by reference herein in its entirety. By placing a connector on the exterior surface of the bone, such devices leave the connector exposed to soft tissues, which can lead to sensitivity, or potential pain if the area is bumped sufficiently to cause the soft tissue to strike the connector or to cause other complications. The prior art is thus characterized by several disadvantages that are addressed by the present invention. The present invention minimizes, and in some aspects eliminates, the above-mentioned failures, and other problems, by utilizing the methods and structural features described herein.

BRIEF SUMMARY AND OBJECTS OF THE INVENTION

It is therefore an object of the present invention to provide a ligament graft or tendon graft attachment system that is simple in design and manufacture.

It is another object of the present invention to provide such a ligament graft attachment system that can be used with any graft substitute.

It is an additional object of the present invention to provide such a ligament graft system in which the graft fixation strength is not dependent on the cancellous bone density of the bone.

It is a further object of the present invention to provide such a ligament graft attachment system that enables the tension of the ligament graft to be adjusted.

It is an additional object of the present invention to provide such a system that can be completely recessed into the bone.

It is another object of the present invention, in accordance with one aspect thereof, to provide a ligament graft attachment system that may be inserted and attached through a hole drilled in the bone, without fully inserting a component into the joint.

It is yet another object of the invention, in accordance with one aspect thereof, to provide a ligament graft attachment system that uses a stepwise interference fit to adjust the ligament graft tension.

The above objects and others not specifically recited are realized in a specific illustrative embodiment of an endosteal tibial ligament fixation system with adjustable tensioning. A grasping hook located on a shaft is used to draw a ligament graft into a contoured drill hole formed in a bone. A series of slanted ridges on the shaft can pass in only one direction through a securing push nut residing in the contoured drill hole, resulting in a interference fit that secures the attachment system, while allowing the tension of the ligament graft to be adjusted.

One advantage of the invention device is that it accommodates all currently know graft substitutes, bone patellar tendon bone, Achilles tendon bone, central quad tendon, and hamstring tendons. This device also anticipates the eventual development of an artificial ligament which would have a closed loop at the tibial end. Thus this device would be suitable for every ACL/PCL surgeon.

Additional objects and advantages of the invention will be set forth in the description which follows, and in part will be apparent from the description, or may be learned by the practice of the invention without undue experimentation. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION OF THE INVENTION

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

The publications and other reference materials referred to herein to describe the background of the invention and to provide additional detail regarding its practice are hereby incorporated by reference herein. The references discussed herein are provided solely for their disclosure prior to the filing date of the present application. Nothing herein is to be construed as a suggestion or admission that the inventor is not entitled to antedate such disclosure by virtue of prior invention.

It must be noted that, as used in this specification and the appended claims, the singular forms "a," "an," and "the" include plural referents unless the context clearly dictates otherwise.

In describing and claiming the present invention, the following terminology will be used in accordance with the definition set out below.

"Interference fit" as used herein shall refer to the concept of a connection between two members in which a portion of one member abuts some portion of the other member in a manner that contactably blocks the separation of the two members.

Applicant has conceived of a system and methods for attaching a ligament graft to the endosteal portion of a bone where the strength of the attachment is independent of the cancellous bone density, and the tension on the ligament may be adjusted. Further, this system may be used with any available ligament or tendon graft.

The present invention adds to the ability of a surgeon to use endosteal technology in such a fashion that tension to the ligament construct can be added in an easily quantifiable and adjustable manner. It is well known that the bone density of the tibial varies widely dependent upon age, weight, and gender of the subject. The mechanism by which fixation is achieved by this inventive device is such that graft fixation strength is not dependent upon the density of the tibial cancellous bone.

Figure 1:
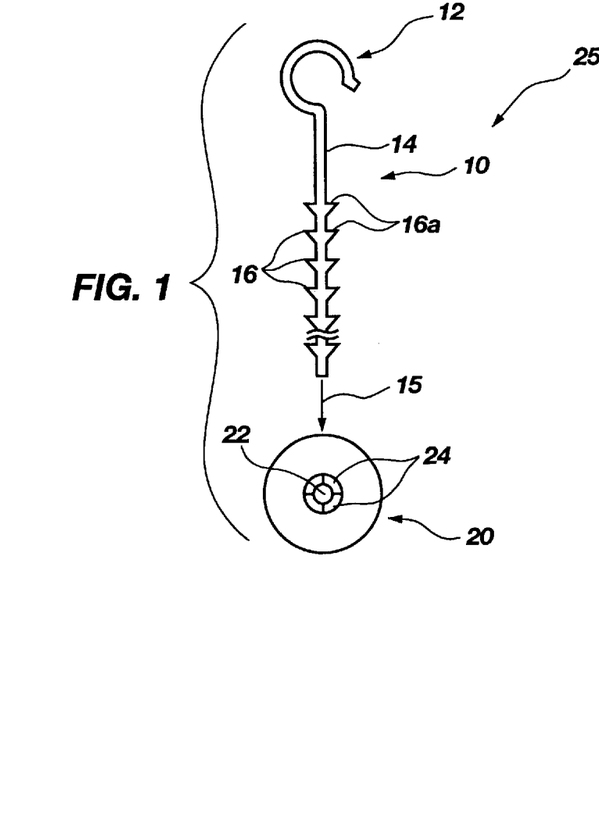
FIG. 1 is a schematic view of a ligament attachment system made in accordance with the principles of the present invention.
Figure 1A:
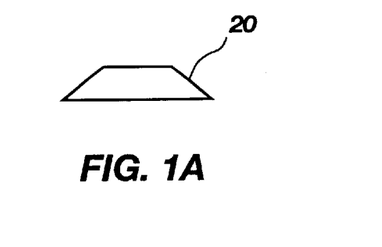
FIG. 1A is a side view of a push nut shown in FIG. 1.
Figure 2:
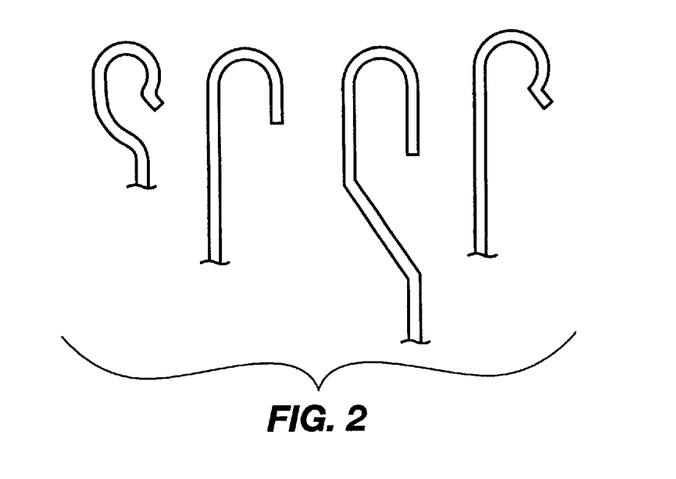
FIG. 2 is a side view of some additional embodiments of a hook portion of the system of FIG. 1.

Referring now to FIG. 1, there is depicted a side view of a first embodiment of a ligament attachment system designated generally at 25, made in accordance with the principles of the present invention. The system includes an attachment member 10, and a retention disc 20. The attachment member 10 includes a grasping hook 12 located on a shaft 14. Grasping hook 12 may be used to grasp a segment of a ligament graft, as will be explained further below. The grasping hook 12 of FIG. 1 is a circular hook forming at least 60% of the arc length of a circle. Turning to FIG. 2, there are shown four different alternative embodiments for the shape of the grasping hook 12 in relation to the shaft 14. These include the asymmetrical loop hook 30, among other embodiments. It will be appreciated that these embodiments are merely some of a number of alternative embodiments for the grasping hook 12, and that all such embodiments capable of grasping a ligament graft in the manner described herein fall within the scope of the present invention. Note how in symmetrical loop hook embodiment 32 the loop forms a circular portion having less than 50% of the arc length of a circle. It will be further appreciated that the grasping hook 12 as disclosed and discussed herein is an example of a grasping means for grasping a ligament graft segment, as discussed below, and that all such grasping means are included within the scope of the present invention.

Returning to FIG. 1, disposed on the shaft 14 are a number of preferably frusto-conical ridges 16. These ridges 16 may assume some shape other than frusto-conical. It will be appreciated that the shaft 14 and grasping hook 12, as shown in FIG. 1, have a round cross section, but that a shaft and hook with any cross sectional conformation can be used and is within the scope of the present invention.

As shown in FIG. 1, a push nut 20 contains a central hole 22, surrounded by a number of preferably flexible flanges 24. While it is preferred that the push nut 20 have four flanges 24, as shown in FIG. 1, a greater or lesser number of flanges may be used. When the shaft 14 of the attachment member 10 is inserted into the central hole 22 of the push nut in a direction indicated by arrow 15, the frusto-conical ridges 16 may pass through the flanges along their slanted sides, but are prevented from returning through the push nut in the opposite direction by an interference fit formed between the wide base 16*a* of the slanted ridges 16 and the flanges 24. As the shaft 14 is further passed through the push nut 20 in the direction of arrow 15, the interference fit is tightenably maintained at each successive ridge 16 that passes through central hole 22. The interference fit thus may be moved stepwise along the length of the shaft 14. It will be appreciated that the shaft 14 may have any number of ridges 16 located along its length. It will be appreciated that the ridges 16, thus act as one example of a locking means, and the flanges 24 act as one example of a receiving means in forming an interference fit. Other possible embodiments that are readily ascertainable, now or in the future, to those skilled in the art to accomplish a stepwise interference fit may be used and are within the scope of the present invention.

The attachment member 10 and push nut 20 may be fashioned of any suitable bio-compatible material including metal, such as titanium, stainless steel, cobalt-chromium-molybdenum alloy, titanium-aluminum vanadium alloy, or other alloys thereof, or of a plastic such as an ultra high molecular weight polyethylene, or of a bio-absorbable material such as poly L-lactic acid.

Figure 3:
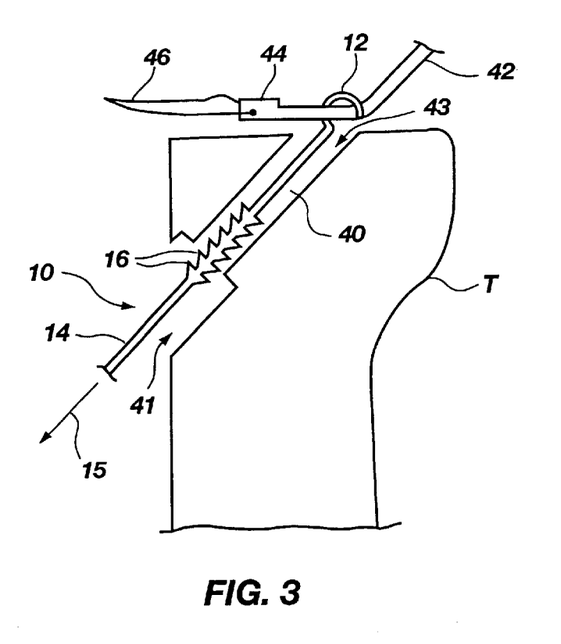
FIG. 3 is a side view of the hook portion of the system of FIG. 1, shown in operation for attaching a ligament graft to a bone.

Turning now to FIG. 3, the embodiment of FIG. 1 is shown being inserted for use in attaching a ligament graft to a bone T, preferably the tibia. It will be appreciated that the present invention may be used in any suitable animal or human patient, and that it may be used for attachment of a ligament graft to any suitable bone, but the preferred usage discussed herein is for attachment of a ligament graft to a human tibia.

As shown in FIG. 3, a through-bore or drill hole 40 has been bored through the endosteal portion of the bone T. It is preferred that the drill hole 40, be a contoured drill hole having a larger diameter portion 41 opposite the narrower receiving insertion portion 43 of the hole 40 for receiving the ligament graft 42.

A ligament graft 42 is attached at one end to the appropriate anatomical structure, such as the femur. Any suitable ligament graft may be used, including a bone patellar tendon bone implant (BTB), an Achilles tendon bone implant, a central quad tendon implant, a hamstring tendon implant, an artificial ligament material, or any other suitable ligament graft known now or in the future to those skilled in the art. The ligament graft depicted in FIG. 3 is a BTB graft, including a bone plug 44. A suture 46 has been attached to the bone plug 44 to aid in the manipulation of the ligament graft 42. The attachment member 10 is inserted into the large diameter portion 41 of drill hole 40, until the grasping hook 12 protrudes from the narrower receiving portion 43 of hole 40 in bone T. The attachment member 10 and suture 46 are manipulated to cause the grasping hook 12 to capture the ligament graft 42, as shown. The attachment member 10 is then drawn back in the direction of arrow 15, thereby drawing the ligament graft 42 into the receiving portion of drill hole 40, looped around grasping hook 12.

Figure 4:
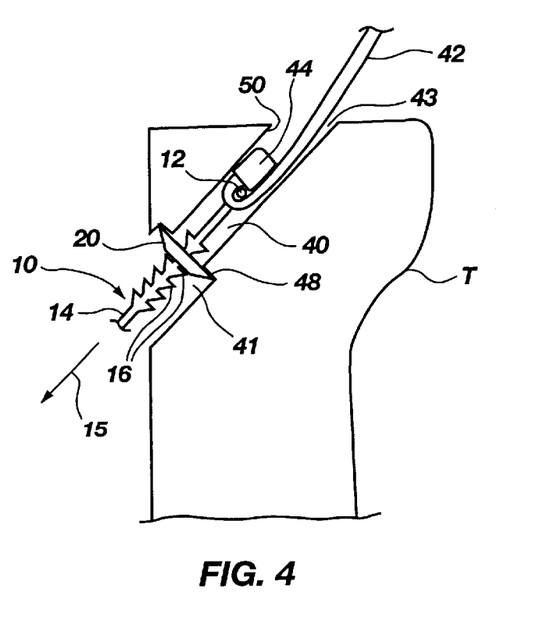
FIG. 4 is a side view of the system of FIG. 1 in an implanted position, thereby operating to attach a ligament graft to the tibia bone.

Referring now to FIG. 4, the position of the ligament graft 42 within the drill hole 40 and the securing of the attachment member 10 are shown. The ligament graft 42 has been drawn into the drill hole 40, looped around the grasping hook 12. Where the ligament graft 42 is a BTB graft, this can result in a flipped BTB attachment, gaining the advantages of such a procedure. The bone plug 44 is compressed between the ligament graft 42 and the wall 50 of the drill hole 40. As can be readily understood by those having ordinary skill in the art, one advantage of the present system over the prior art is the ability of the attachment member 10 to securely hold either the internal or external (cancellous or cortical) face of the bone plug 44 against the wall 50. This allows for the use of BTB grafts that could not be attached with cannulated screws. The ligament graft 42 is thus connected to the endosteal portion of the bone T.

In FIG. 4, the attachment member 10 has been secured in place with the push nut 20. The shaft 14 was inserted through the central hole 40 and the push nut 20 moved up the shaft 14 and against an annular retaining wall 48, formed by the larger diameter portion 41 of the drill hole 40. The shaft 14 may then be further withdrawn through the push nut 20 in the direction of arrow 15, to thereby increase the tension on the ligament graft 42. As the shaft 14 is withdrawn, the interference fit is maintained in a suitable manner. This allows for the tension on the ligament graft 42 to be adjusted, and allows the system to accommodate variations from the ideal ligament graft 42 length.

When the ligament graft 42 has reached the desired tension, the portion of the shaft 14 protruding from the larger diameter portion 41 of drill hole 40 is preferably cut off, thereby causing the entire system 25 to reside within the drill hole 40 of the bone T. Patella P is also shown.

Figure 5:
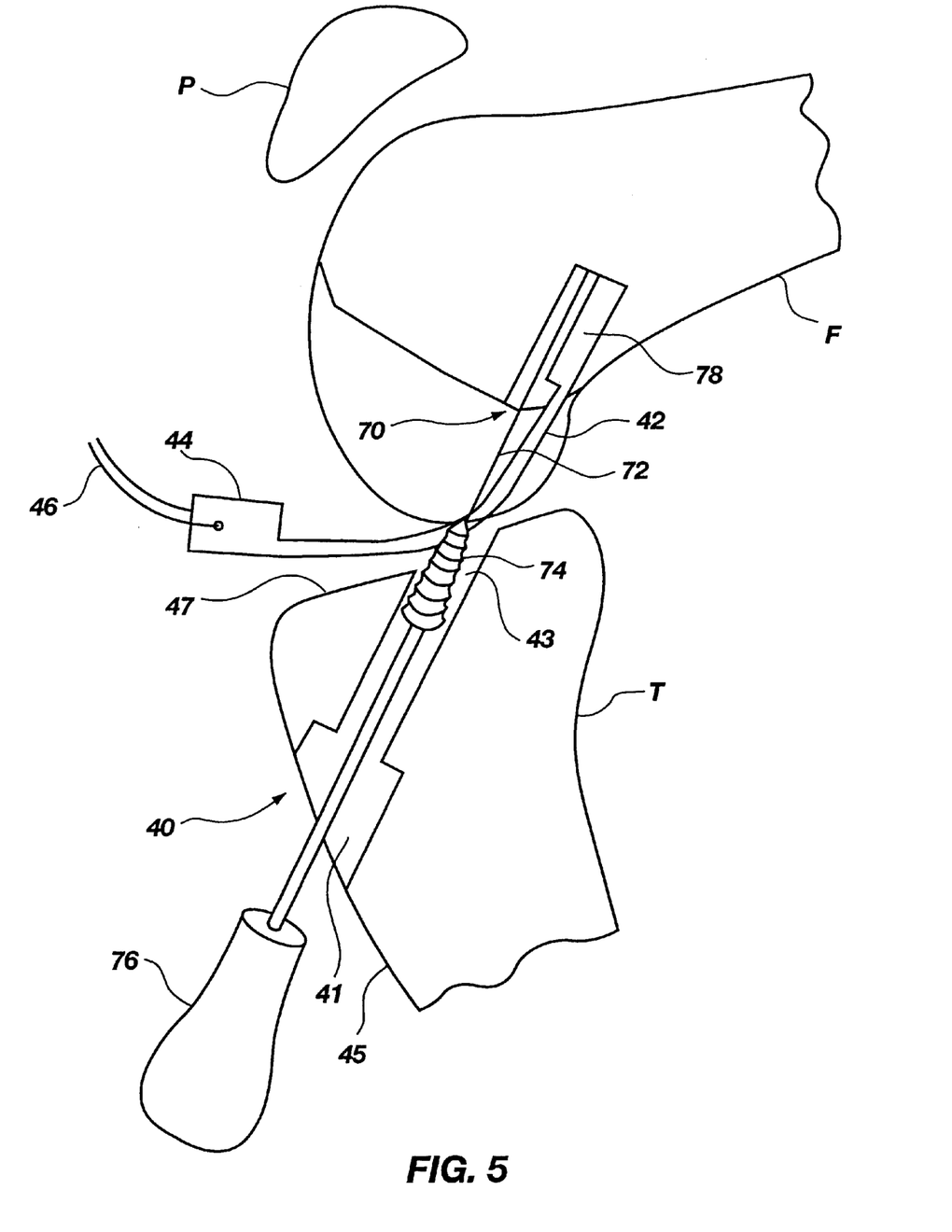
FIG. 5 is a side view of an interference screw utilizing a transtibial pathway to achieve femoral fixation of a ligament graft.
Figure 5A:
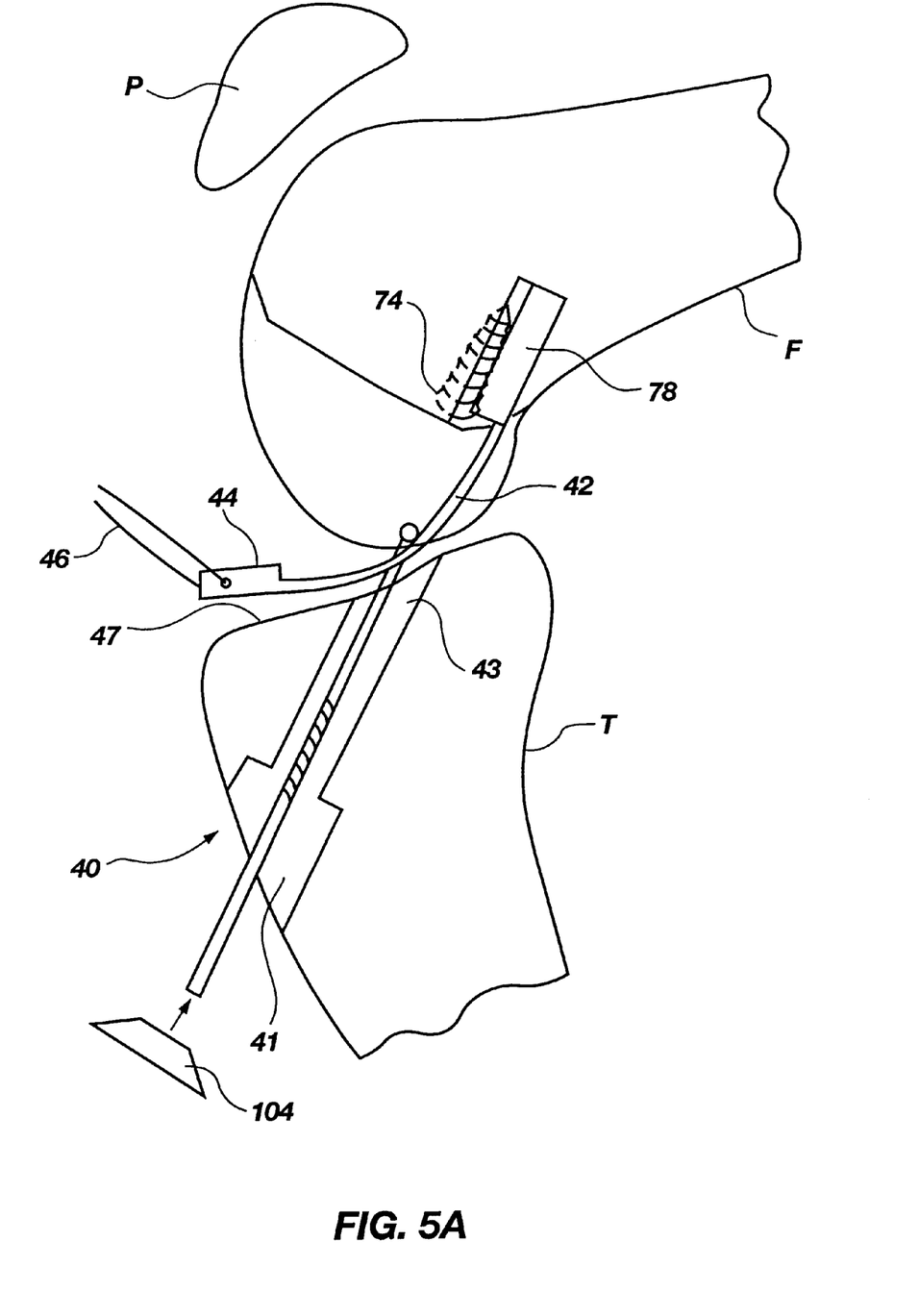
FIG. 5A is a side view of the interference screw of FIG. 5 in an implanted position.

Referring now to FIGS. 5 and 5A, in FIG. 5 is shown a side view of a method of attaching the distal end of a ligament graft 42 for use across a joint, in preparation for use of the system 25 (not shown in FIG. 5) of the present invention or an alternative version as shown. As shown in FIG. 5, the preferred embodiment is a human knee joint, but it will be appreciated the method may be used with any suitable joint. The knee joint is flexed to an appropriate angle. A contoured drill hole 40 is bored from an anterior surface 45 of the tibia bone T to the upper surface 47 of the tibia, also at the desired angle. A drill hole 70 is bored in the femur 12, in suitable alignment with the contoured drill hole 40.

A ligament graft 42 is inserted into the drill hole 70. This graft may be a BTB graft, as depicted in FIG. 5, or it may be a hamstring graft, or any other suitable ligament graft. A guide wire 72 is inserted in drill hole 70, to facilitate the securing of the ligament graft 42. The guide wire 72 extends from the drill hole 70, into the contoured drill hole 40. A screw 74, preferably a cannulated screw, is then inserted into the larger diameter portion 41 of the contoured drill hole 40, and passed through the narrower portion 41 of the contoured drill hole 40, across the knee joint and into the drill hole 70. The guide wire 72 is used to position the screw 74. The screw 74 is then advanced into the hole 70 using a driver 76 to engage the walls of hole 70 and compress the ligament graft 42 against said walls. In procedures such as that depicted in FIG. 5, in which a BTB graft is used, the screw 74 compresses against the bone plug 78 of the ligament graft 42. Once the ligament graft 42 is secured to the femur by the screw 74, it may then be secured to the tibia using the attachment member 10 and retention disc 20, as described above in conjunction with FIGS. 1–4.

Figure 6:
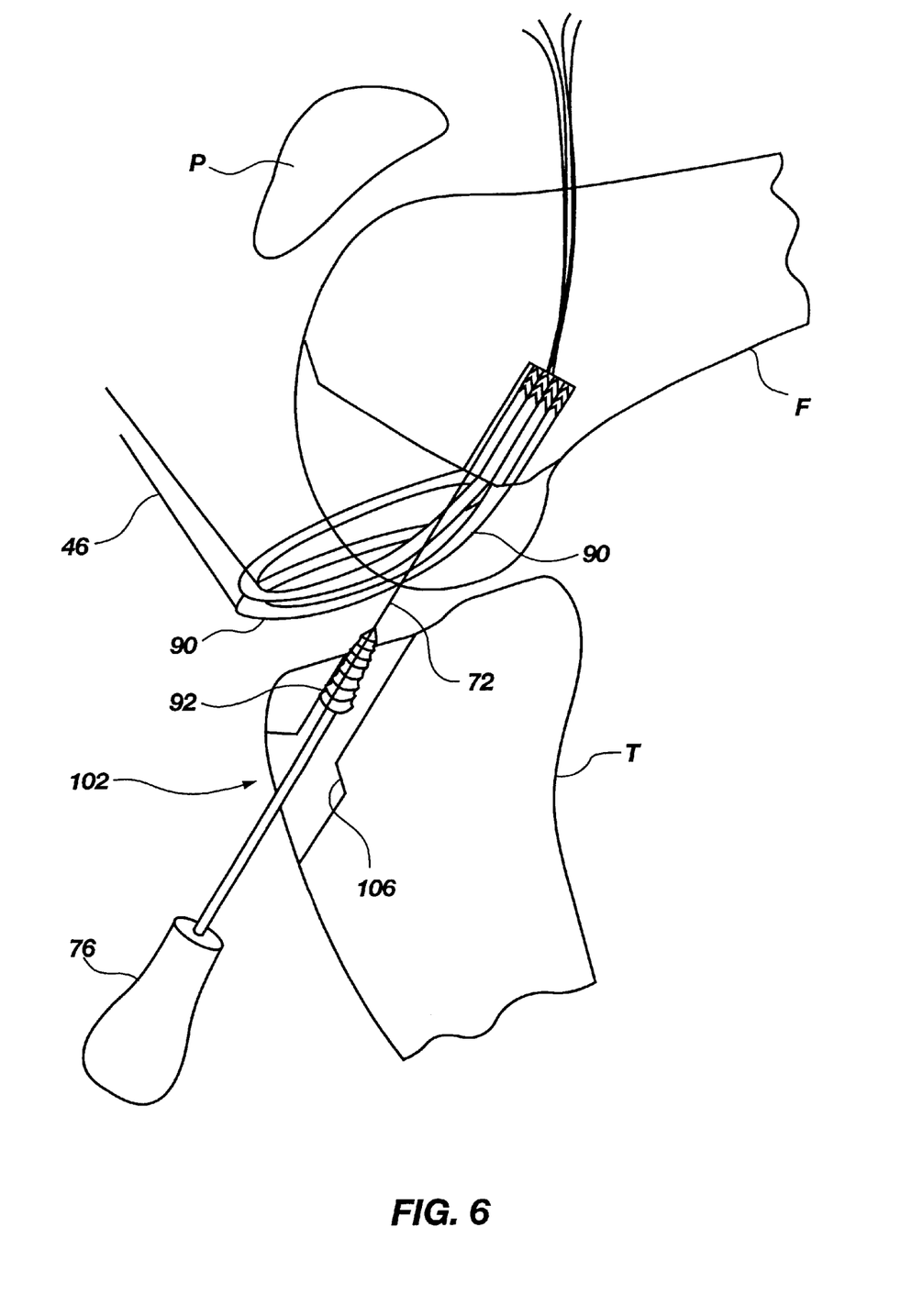
FIG. 6 is a side view of an interference screw utilizing a transtibial pathway to achieve femoral fixation of a hamstring ligament graft.
Figure 6A:
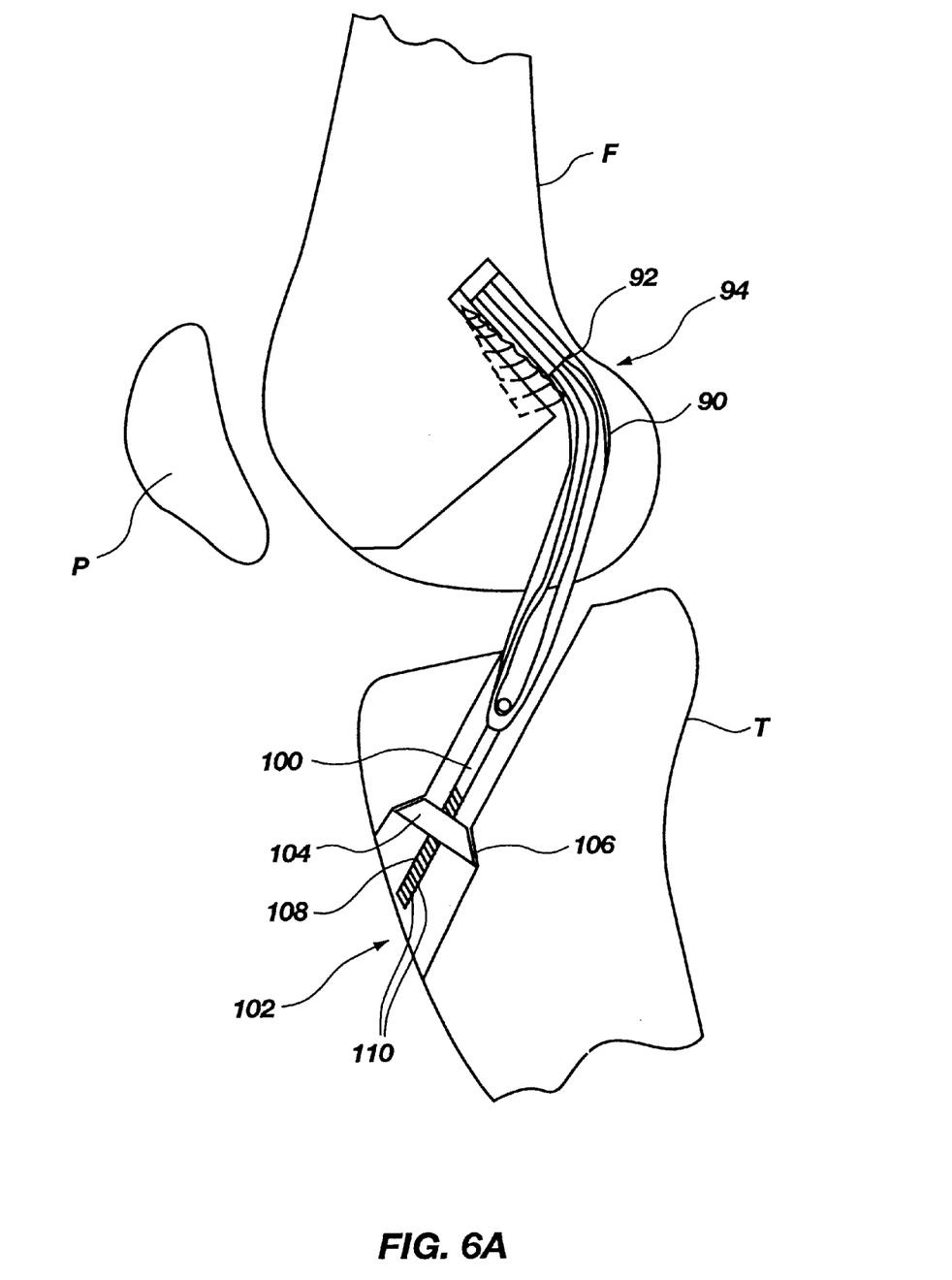
FIG. 6A is a side view of an alternative embodiment of a ligament attachment system made in accordance with the principles of the present invention, in position for attachment of a ligament graft reconstructing an ACL.

FIGS. 6 and 6A depict a ligament graft for ACL reconstruction, disposed in place with interference screw 92 in a human knee joint and attached to the endosteal portion of the tibia T, using another embodiment (shown in FIG. 6A) of an attachment system made in accordance with the principles of the present invention. A ligament graft 90 is attached to the femur F, using a screw 92 to compress the graft 90 against the wall of a drill hole 94. Note that ligament graft 90 is depicted as a hamstring ACL graft, illustrating that the present system may be used with any ligament graft. An attachment member 100 has been used to capture the graft 90 and draw it into the contoured drill hole 102. The attachment member 100 was then secured using a preferably frusto-conical retention disc 104 which seats against slanted wall 106 of the contoured drill hole 102. Note that retention disc 104 has a preferably frusto-conical or slanted structure that matches the slanted wall 106. The matching of the shape of the retention disc 104 to the shape of the wall 106 increases the strength of the attachment of the ligament graft 90. It will be appreciated that this slanted structure is merely one of many possible matching shape interactions, and all such interactions are within the scope of the present invention.

In the embodiment of FIG. 6A, the shaft 108 of the attachment member 100 is threaded, rather than having the slanted ridges 16 of FIGS. 1–4. The retention disc 104 has a threaded central hole that turns on the threads 110 of the shaft 108. Tension in the ligament graft 90 tension is adjustable by the turning of the retention disc 104.

Figure 7:
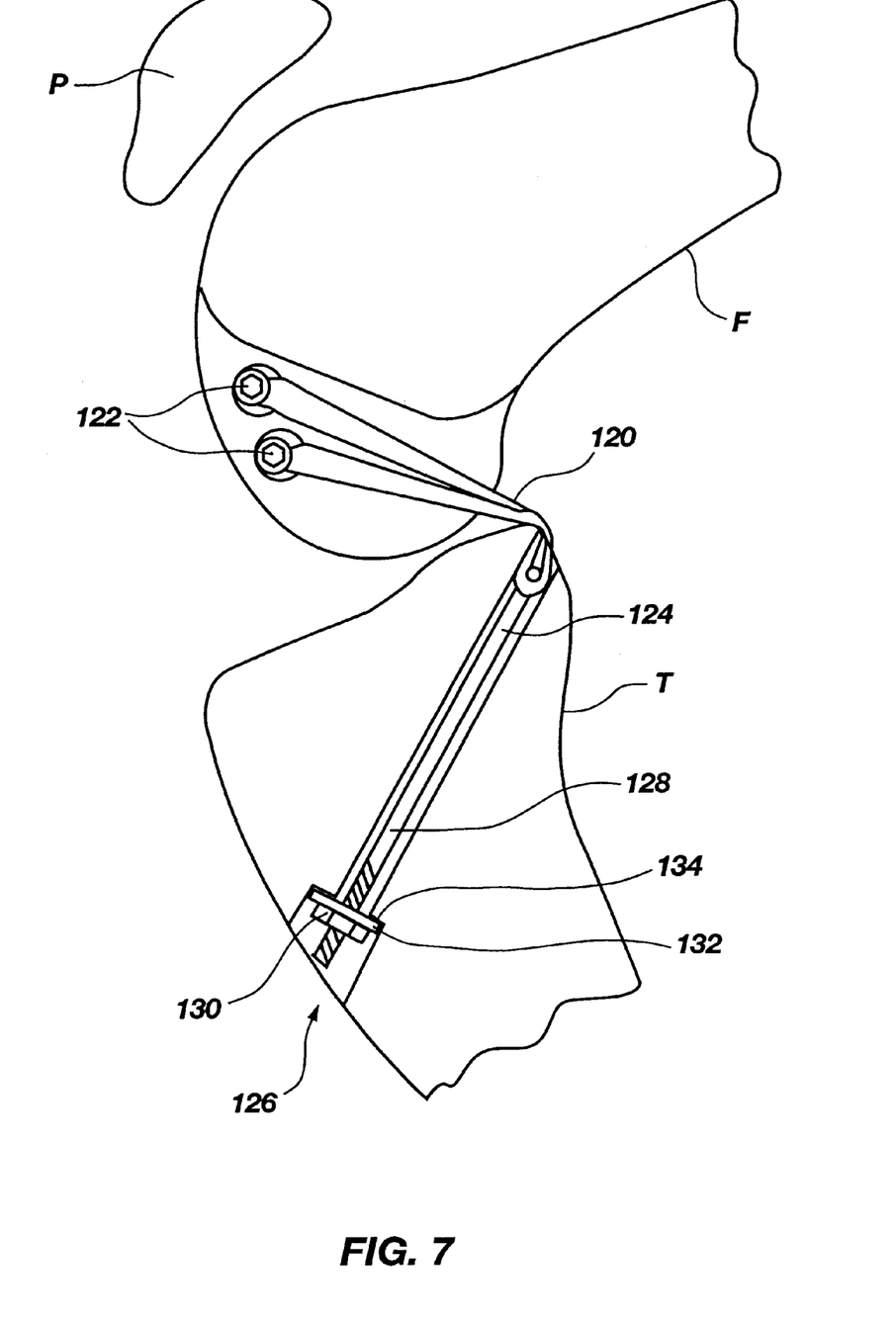
FIG. 7 is a side view of another embodiment of a ligament attachment system made in accordance with the principles of the present invention, in position for attachment of a ligament graft reconstructing a PCL.

Referring now to FIG. 7, there is depicted an additional embodiment of a system made in accordance with the principles of the present invention, as used to secure a ligament graft 120 in a posterior cruciate ligament (PCL) reconstruction surgery. The ligament graft 120 may be any suitable graft, and is shown attached to the femur F in traditional fashion using screws 122, but may, of course, be secured in any suitable manner, such as by a bone screw within a bone. The graft 120 was captured by an attachment hook member 124, in the manner described above and drawn into the contoured drill hole 126 to be secured inside the endosteal portion of the tibia T. Note that the contoured drill hole 126 extends from the anterior to the posterior of the tibia T, at an appropriate angle.

The attachment member 124 is secured within the contoured drill hole 126 by the attachment of a nut 130 to the threaded shaft 128 of the attachment member. A washer 132 is disposed between the nut 130 and an annular retaining wall 134 of the contoured drill hole. The washer prevents the rotation of the nut 130 from damaging the annular retaining wall 134.

Tension on the ligament graft 120 may be measured and adjusted by turning the nut 130. While the nut 130 may be any appropriate threaded attachment device, it is preferred to use a suitable hex nut as known in the art. It is preferred that the washer 132 be a plate washer, but any suitable washer may be used. It is further preferred that the plate washer 132 be fashioned of sheet metal. The nut 130 and washer 132 are another example of a securing means for securing the attachment member 124.

Figure 8:
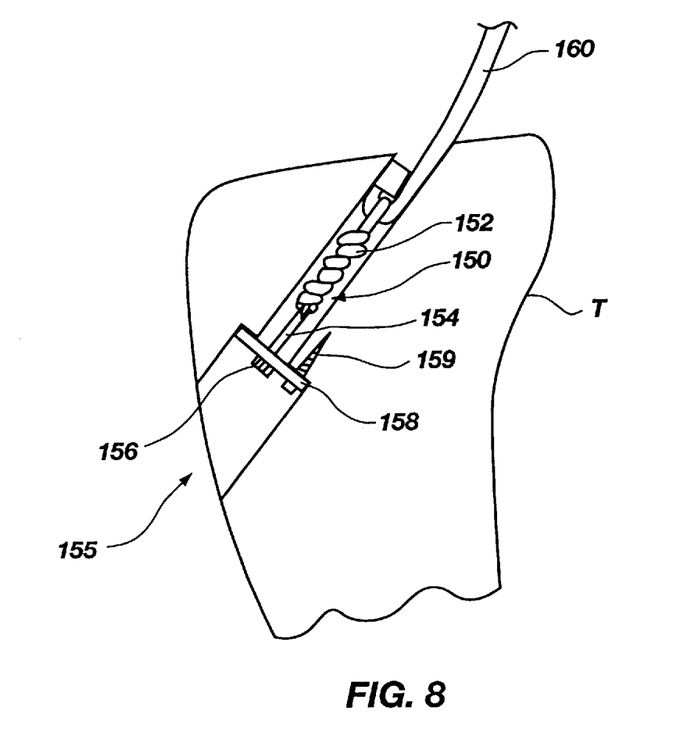
FIG. 8 is a side view of another embodiment of a ligament attachment system, made in accordance with the principles of the present invention.
Figure 8A:
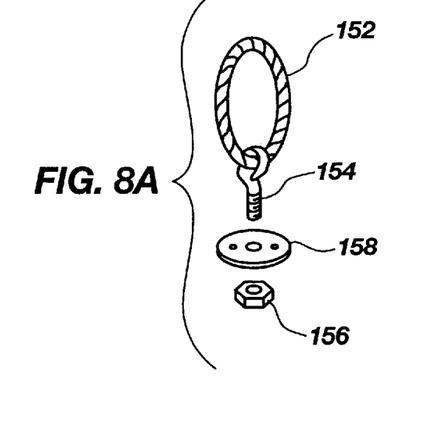
FIG. 8A is an exploded view of the eyebolt and retention disc member with a flexible tension strand, shown in FIG. 8.
Figure 8B:
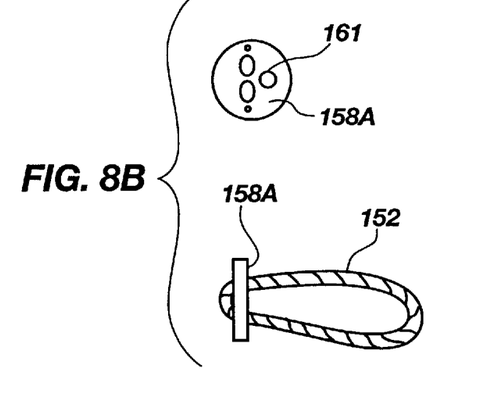
FIG. 8B is a side view of an alternative embodiment of the features shown in FIG. 8A.

FIG. 8 depicts yet another embodiment of a system for attaching a ligament graft to a bone, in accordance with the principles of the present invention. This embodiment features an attachment member 150 that includes a flexible strand 152. The flexible strand 152 is preferably a continuous loop. The strand 152 is attached to an eyebolt 154 and serves as the grasping means for capturing a ligament graft 160. The strand 152 may alternatively be looped and attached directly to retention disc 158A, as shown in FIG. 8B.

When the attachment member is disposed in contoured drill hole 155, grasping ligament graft 160. The attachment member is fixedly attached to a retention disc 158, such as with an optional locking nut 156 or in any other suitable manner. The retention disc 158 may be rotated to twist the flexible strand 152 as shown, and thereby adjust the tension of the ligament graft 160. When the desired tension is reached, the disc may be secured by insertion of a fixation screw 159 into the bone T as shown, to prevent untwisting of the strand 152. The fixation screw 159 may be placed through the body of the retention disc 158, or through a fixation hole 161 formed in the retention disc, such as disk 158A of FIG. 8B.

It will be appreciated that additional embodiments of the continuous loop flexible strand embodiment of FIG. 8 are possible, including embodiments in which the strand 152 is directly connected to the retention disc 158, such as by passing through holes formed in the disc 158.

Figure 9:
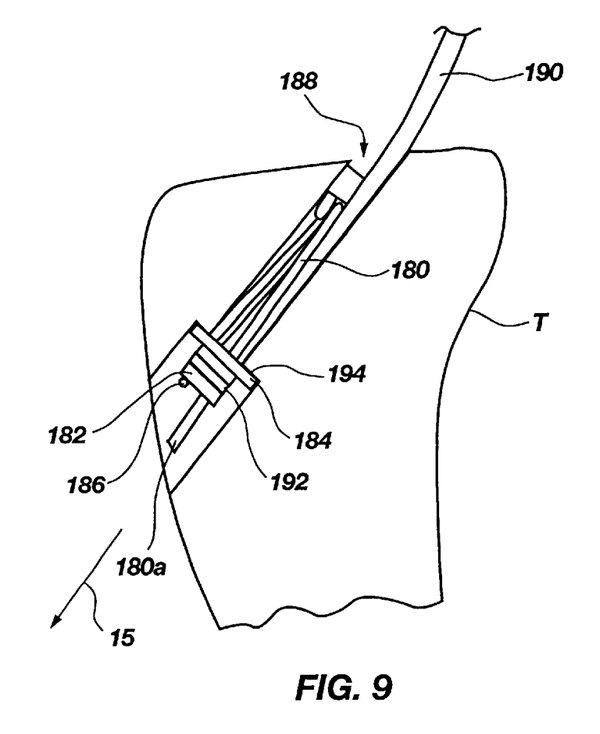
FIG. 9 is a side view of an additional embodiment of a ligament attachment system, made in accordance with the principles of the present invention.
Figure 9A:
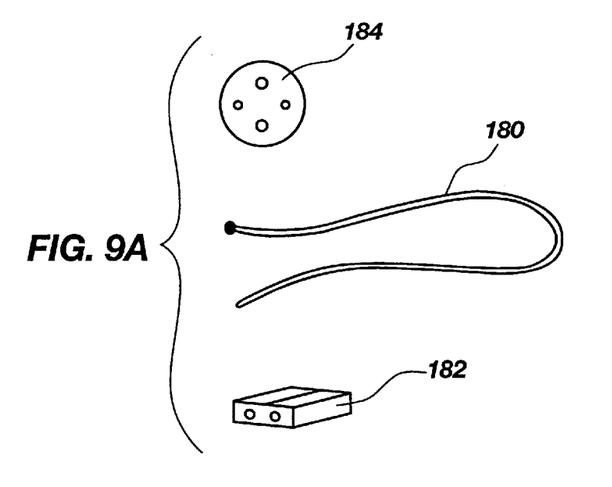
FIG. 9A is an exploded view of the e, cable collector and retention disc combination shown in FIG. 9.

FIG. 9 depicts a flexible strand embodiment that utilizes a cable 180 as the capture means. The cable is passed through a passage in a cable collector 182, then through a hole in a retention disc 184. It is preferred that the cable 180 have one enlarged end that prevents the cable from passing entirely through the cable collector 182. In the FIG. 9 embodiment this is accomplished by the bead 186.

The free end 180a of cable 180 is used to capture a ligament graft 190 and draw the graft 190 into a contoured drill hole 188. The cable 180 passes back through a second hole in the retention disc 184 and a second passage in the cable collector 182. The cable 180 may be inserted back through the disc 184 and collector 182 prior to, or after, capture of the ligament graft 190.

Tension of the ligament graft 190 may be measured in any suitable manner known to those having ordinary skill in the art, (such as by coupling the device with a tension measuring apparatus to measure the tension within the graft 190 precisely). The tension may be adjusted by retension of the free end 180a to thereby shorten the cable 180. The retention disc 184 secures the attachment member cable 180 in place by abutting against the annular retaining wall 194 of the contoured drill hole 188. When a desired tension is reached, the cable 180 is secured. In the embodiment of FIG. 9, this has been accomplished by crimping the cable collector 182, thereby preventing the cable 180 from withdrawing from its tension position, as shown by crimp mark 192 The remaining length of the cable 180 may then be removed, placing the entire ligament attachment structure within the bone T.

In accordance with the features and combinations described above, a preferred method of attaching a ligament or tendon implant to the endosteal portion of a bone includes the steps of:

(a) drilling a hole through the bone of a patient;

(b) attaching the implant to another anatomical structure;

(c) inserting through the hole an attachment member comprising a grasping hook, configured for grasping a free end of the ligament or tendon implant;

a shaft attached to the grasping hook, the shaft configured to interact with a securing means, and the shaft and grasping hook adapted to fit within a hole in said bone;

(d) grasping the free end of the implant with the grasping hook;

(e) pulling the implant into the hole;

(f) securing the shaft to a securing means, such that the implant is retained within the hole.

It is further preferred to drill a contoured hole having a larger diameter portion and a narrower diameter portion as described, such that the securing mechanisms as disclosed herein can be used in the above method. Any known ligament graft material may be used.

In accordance with the features and combinations described above, another preferred method of attaching a ligament or tendon implant to the endosteal portion of a bone includes the steps of:

(a) drilling a hole through the bone of a patient;

(b) attaching the implant to another anatomical structure;

(c) inserting through the hole an attachment member comprising a grasping means for grasping the ligament or tendon implant;

a shaft attached to the grasping means, the shaft and grasping means adapted to fit within a hole in said bone, the shaft further comprising a locking means disposed on the shaft;

(d) grasping the free end of the implant with the grasping means;

(e) pulling the implant into the hole;

(f) inserting the shaft into a securing means having a receiving means for interacting with the locking means of the shaft to thereby inhibit movement of said attachment member relative to the bone in a first direction; and (g) inserting the shaft into the securing means until the implant is subjected to a predetermined tension.

It is preferred to drill a contoured hole with a larger diameter portion, such that the securing mechanisms as disclosed herein can be used in the method. It is further preferred that the securing means be disposed to attach to the shaft of the attachment member. It is also preferred that the first direction is opposite the direction in which the attachment member is inserted. Any known ligament graft material may be used.

Another preferred method of attaching a ligament or tendon implant to the endosteal portion of a bone includes the steps of:

(a) drilling a hole through the bone of a patient;

(b) attaching the implant to another anatomical structure;

(c) inserting through the hole an attachment member comprising a flexible grasping means, configured for grasping a free end of the ligament or tendon implant;

a tensioning means attached to the flexible grasping means, the tension means configured to adjust the tension of the implant when the grasping means is attached to the implant and disposed in a hole located inside said bone;

(d) grasping the free end of the implant with the flexible grasping means;

(e) pulling the implant into the hole;

(f) adjusting the tension of the implant to a predetermined tension by activating the tensioning means; and (g) securing the tensioning means to the bone.

The flexible grasping means may comprise a flexible continuous loop attached to the tensioning means, or a flexible strand that may be attached to the tensioning means, or any suitable means for accomplishing the function described.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A device for the fixation of a ligament or tendon implant to a bone of a patient comprising:

an ultra high molecular weight polyethylene ligament attachment member comprising a grasping hook configured for grasping a free end of the ligament or tendon implant, a shaft attached to the grasping hook, and a series of slanted ridges formed along the long axis of the shaft, the ligament attachment member adapted to fit within a contoured drill hole in said bone;

an ultra high molecular weight polyethylene push nut for securing the ligament attachment member to the bone, disposed to attach to the shaft of the ligament attachment member when the shaft is inserted into the push nut, the push nut further comprising one or more flanges surrounding a central hole, the flanges configured to allow slanted ridges on the shaft to pass in one direction when the shaft is inserted into the central hole, but engaging the slanted ridges in an interference fit when the shaft is moved in an opposite direction to thereby inhibit movement of said ligament attachment member relative to the bone in a direction opposite the direction in which the shaft is inserted as the push nut is secured against an annular ledge of the contoured drill hole in the bone, where a larger-diameter portion of the contoured drill hole is connected to a narrower-diameter portion of the contoured drill hole, and the entire device remains inside an endosteal portion of said bone; wherein said grasping hook is an open loop with an open portion;

wherein said grasping hook has a circular shape forming at least 60% of the arc length of a circle;

wherein said grasping hook has a free end portion, said free end portion extending away from said shaft to thereby operate as a guide for guiding said ligament or tendon into said loop;

wherein the push nut has a frusto-conical shape configured to match a frusto-conical shape of a drill hole in the bone to provide an increased contact area between the push nut and the bone; and wherein said grasping hook has a substantially uniform thickness characterized by an absence of a pointed end to prevent said grasping hook from embedding into the bone.

2. A device for the fixation of a ligament or tendon implant to a bone of a patient comprising:

a ligament attachment member, said ligament attachment member being constructed from a material selected from the group consisting of titanium, cobalt-chromium-molybdenum alloy, cobalt-chromium alloy, titanium-aluminum vanadium alloy, titanium-aluminum alloy and a bio-absorbable material, said ligament attachment member comprising a grasping hook configured for grasping a free end of the ligament or tendon implant, a shaft attached to the grasping hook, and a series of slanted ridges disposed on the shaft along a long axis of the shaft, the ligament attachment member adapted to fit within a contoured drill hole in said bone;

a push nut for securing the ligament attachment member to the bone, said push nut configured and arranged to attach to the shaft of the ligament attachment member when the shaft is inserted into the push nut, the push nut further comprising one or more flanges surrounding a central hole, the flanges configured to allow slanted ridges on the shaft to pass in one direction when the shaft is inserted into the central hole, but engaging the slanted ridges in an interference fit when the shaft is forced in an opposite direction to thereby inhibit movement of said ligament attachment member relative to the bone in a direction opposite the direction in which the shaft is inserted as the push nut is secured against an annular ledge of the contoured drill hole in the bone, wherein a larger-diameter portion of the contoured drill hole is connected to a narrower-diameter portion of the contoured drill hole, and the entire device remains inside an endosteal portion of said bone;

wherein said grasping hook is an open loop with an open portion;

wherein said grasping hook includes a main portion having a circular shape forming at least a continuous 60% portion of an arc length of a circle such that said main portion extends in a first, circular path;

wherein said grasping hook further includes a free end surface, said free end surface extending away from said shaft along a second, linear path that extends in a different direction than the first, circular path, to thereby operate as a guide for guiding said ligament or tendon into said loop;

wherein the push nut includes a frusto-conical shaped portion configured to match a frusto-conical shape of drill holes in bones to provide potential for an increased contact area between the push nut and the bone;

wherein said shaft and said main portion of said grasping hook each have the same substantially uniform thickness; and wherein the grasping hook consists of a single grasping hook and wherein the main portion of said hook extends from the shaft in said first, circular path to a first location beyond a first side of the shaft and then to a second location beyond a second side of the shaft, such that a proximal portion of the hook resides at the first location and a distal portion of the hook resides at the second location.

3. A system for repairing a joint within an endosteal portion of a bone of a patient, said system comprising:

an implant for attachment to said bone as a ligament or tendon;

an attachment member comprising a grasping hook configured for grasping a free end of the implant, a shaft attached to the grasping hook, and a series of slanted ridges disposed on said shaft along a long axis of the shaft, the attachment member adapted to fit within a contoured drill hole in said bone;

a push nut for securing the attachment member to the bone, disposed to attach to the shaft of the attachment member when the shaft is inserted into the push nut, the push nut further comprising one or more flanges surrounding a central hole, the flanges configured to allow slanted ridges on the shaft to pass in one direction when the shaft is inserted into the central hole, but engaging the slanted ridges in an interference fit when the shaft is moved in an opposite direction to thereby inhibit movement of said attachment member relative to the bone in a direction opposite the direction in which the shaft is inserted as the push nut is secured against an annular ledge of the contoured drill hole in the bone, where a larger-diameter portion of the contoured drill hole is connected to a narrower-diameter portion of the contoured drill hole, and the entire device remains inside said endosteal portion of said bone;

wherein said grasping hook includes a main portion having a circular shape forming at least a continuous 60% portion of an arc length of a circle such that said main portion extends in a first, circular path;

wherein said grasping hook further includes a free end surface, said free end surface extending away from said shaft along a second, linear path that extends in a different direction than the first, circular path, to thereby operate as a guide for guiding said implant into said loop;

wherein the push nut includes a frusto-conical shaped portion configured to match a frusto-conical shape of drill holes in bones to provide potential for an increased contact area between the push nut and the bone;

wherein said shaft and said main portion of said grasping hook each have the same substantially uniform thickness; and wherein the grasping hook consists of a single grasping hook and wherein the main portion of said hook extends from the shaft in said first, circular path to a first location beyond a first side of the shaft and then to a second location beyond a second side of the shaft, such that a proximal portion of the hook resides at the first location and a distal portion of the hook resides at the second location.

* * * * *